United States Patent [19]
Mason et al.

[11] Patent Number: 5,772,618
[45] Date of Patent: Jun. 30, 1998

[54] HINGE FOR AN ORTHOPEDIC BRACE

[75] Inventors: Bradley R. Mason, Olivenhain; Jeffrey T. Mason, Escondido, both of Calif.

[73] Assignee: Breg, Inc., Vista, Calif.

[21] Appl. No.: 656,088

[22] Filed: May 31, 1996

[51] Int. Cl.⁶ ........................................................ A61F 5/00
[52] U.S. Cl. ................................................ 602/16; 602/26
[58] Field of Search .............................. 602/5–8, 16, 29, 602/23, 26

[56] References Cited

U.S. PATENT DOCUMENTS

| | | | |
|---|---|---|---|
| 4,493,316 | 1/1985 | Reed et al. ............................. | 602/26 X |
| 4,620,532 | 11/1986 | Housewerth . | |
| 4,691,697 | 9/1987 | Arensdorf et al. ....................... | 602/16 |
| 4,697,583 | 10/1987 | Mason et al. ............................ | 602/26 |
| 4,991,571 | 2/1991 | Kausek .................................. | 602/26 X |
| 5,038,765 | 8/1991 | Young et al. ............................ | 602/16 |
| 5,062,858 | 11/1991 | Broeck et al. .......................... | 602/16 X |
| 5,168,865 | 12/1992 | Radcliffe et al. ....................... | 602/26 X |
| 5,356,370 | 10/1994 | Fleming ................................. | 602/26 X |
| 5,586,970 | 12/1996 | Morris et al. ............................ | 602/26 |

*Primary Examiner*—Linda C. Dvorak
*Attorney, Agent, or Firm*—Rodney F. Brown

[57] ABSTRACT

A hinge is provided for an orthopedic brace that pivotally couples the ends of upper and lower arms of the brace. The hinge includes a pair of hinge plates, each having a rigid support member enclosed within an inner covering and an outer covering that integrally form a continuous unitary covering providing the hinge plate with a smooth, friction-reduced surface. The ends of the upper and lower arms are positioned between the hinge plates and the plates and ends are interconnected such that the ends of the upper and lower arms rotatably engage the friction-reduced surfaces of the hinge plates.

18 Claims, 6 Drawing Sheets

HINGE FOR AN ORTHOPEDIC BRACE

TECHNICAL FIELD

The present invention relates generally to orthopedic braces, and more particularly to a hinge for an orthopedic brace.

BACKGROUND OF THE INVENTION

Orthopedic braces are worn on the body of a user to stabilize a skeletal joint that has been weakened by injury or other infirmity. Orthopedic braces commonly have rigid structural components that support and stabilize the joint. Typically, the structural components of the rigid brace are dynamically linked together by one or more hinges enabling controlled pivotal movement of the joint during rehabilitative therapy or user activity. The rigid brace is positioned on the body such that the hinges traverse the joint being stabilized, while the rigid components are secured to the body at a plurality of engagement faces above and below the joint.

Figure 1A:
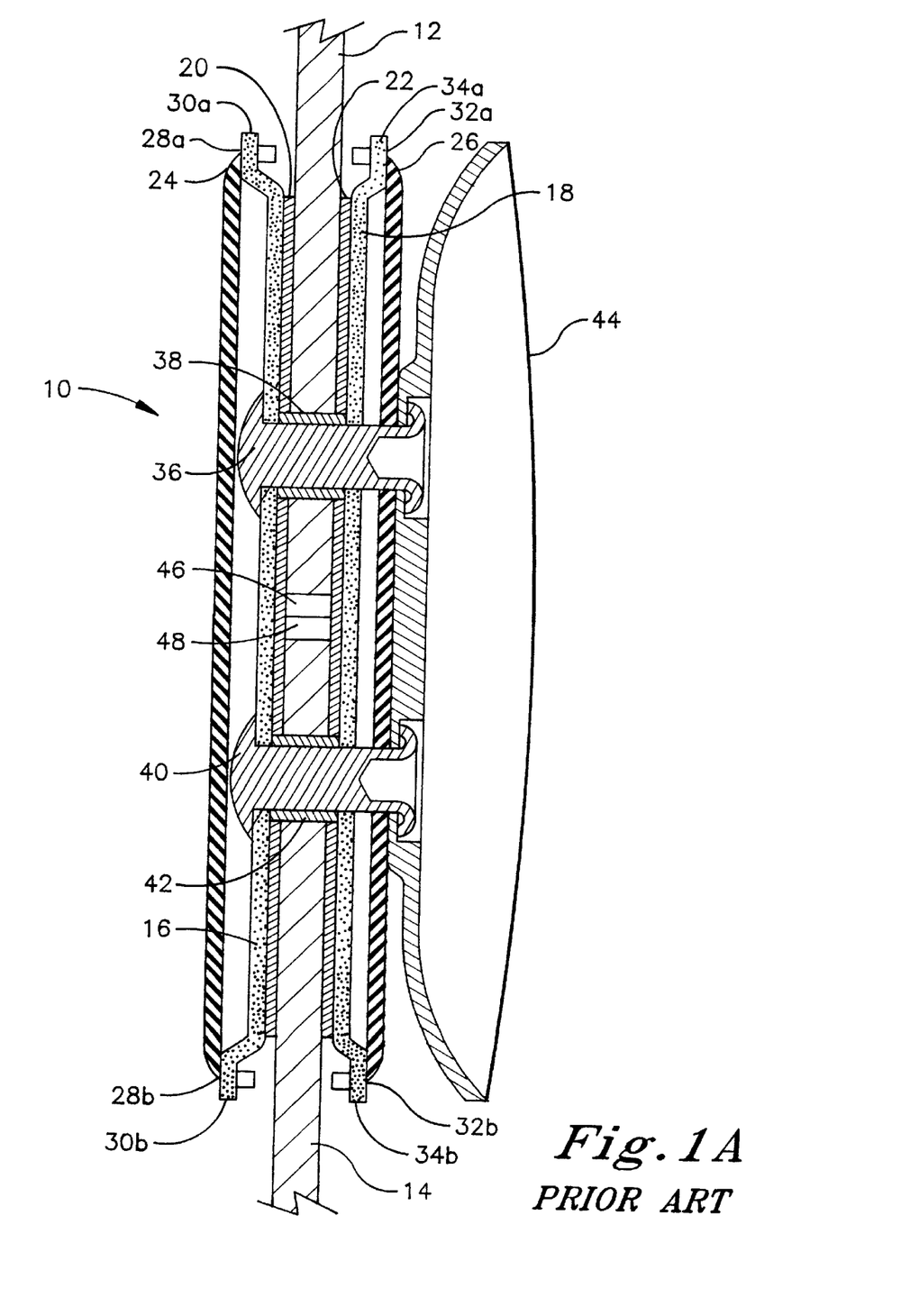
FIG. 1A is a cross-sectional view of a prior art hinge for an orthopedic brace.

Referring to FIG. 1A, a conventional hinge 10 for an orthopedic brace having rigid upper and lower arms 12, 14 is illustrated. The hinge 10 dynamically joins the upper and lower arms 12, 14 for rotational pivoting movement thereof. The hinge 10 includes first and second rigid metal hinge plates 16, 18 that are spaced from the upper and lower arms 12, 14 by friction-reducing plastic washers 20, 22. The washers 20, 22 slidably engage the upper and lower arms 12, 14 during rotational pivoting movement thereof. The conventional hinge 10 further includes first and second substantially rigid hinge covers 24, 26 positioned over the first and second hinge plates 16, 18, respectively, to enclose and protect the internal hinge components, as well as to shield the user and others from contact with the internal hinge components. The first hinge cover 24 has upper and lower slots 28a, 28b formed therein to receive upper and lower flanges 30a, 30b extending from the first hinge plate 16, thereby enabling detachable connection of the first hinge cover 24 to the first hinge plate 16. The second hinge cover 26 similarly has upper and lower slots 32a, 32b formed therein to receive upper and lower flanges 34a, 34b extending from the second hinge plate 18 facilitating connection of the second hinge cover 26 to the second hinge plate 18.

The conventional hinge 10 also includes a rivet fastener 36 and bushing 38 rotatably coupling an upper portion of the first and second hinge plates 16, 18, washers 20, 22 and second hinge cover 26 to the upper arm 12. Another rivet fastener 40 and bushing 42 rotatably couples a lower portion of the first and second hinge plates 16, 18, washers 20, 22 and second hinge cover 26 to the lower arm 14. The rivet fasteners 38, 40 38, 40 also attach a hinge pad holder 44 to the hinge 10. The hinge 10 is further provided with intermeshing teeth 46, 48 located on adjacent ends of the upper and lower arms 12, 14 to maintain symmetric movement of the upper and lower arms 12, 14 relative to the hinge 10.

Figure 1B:
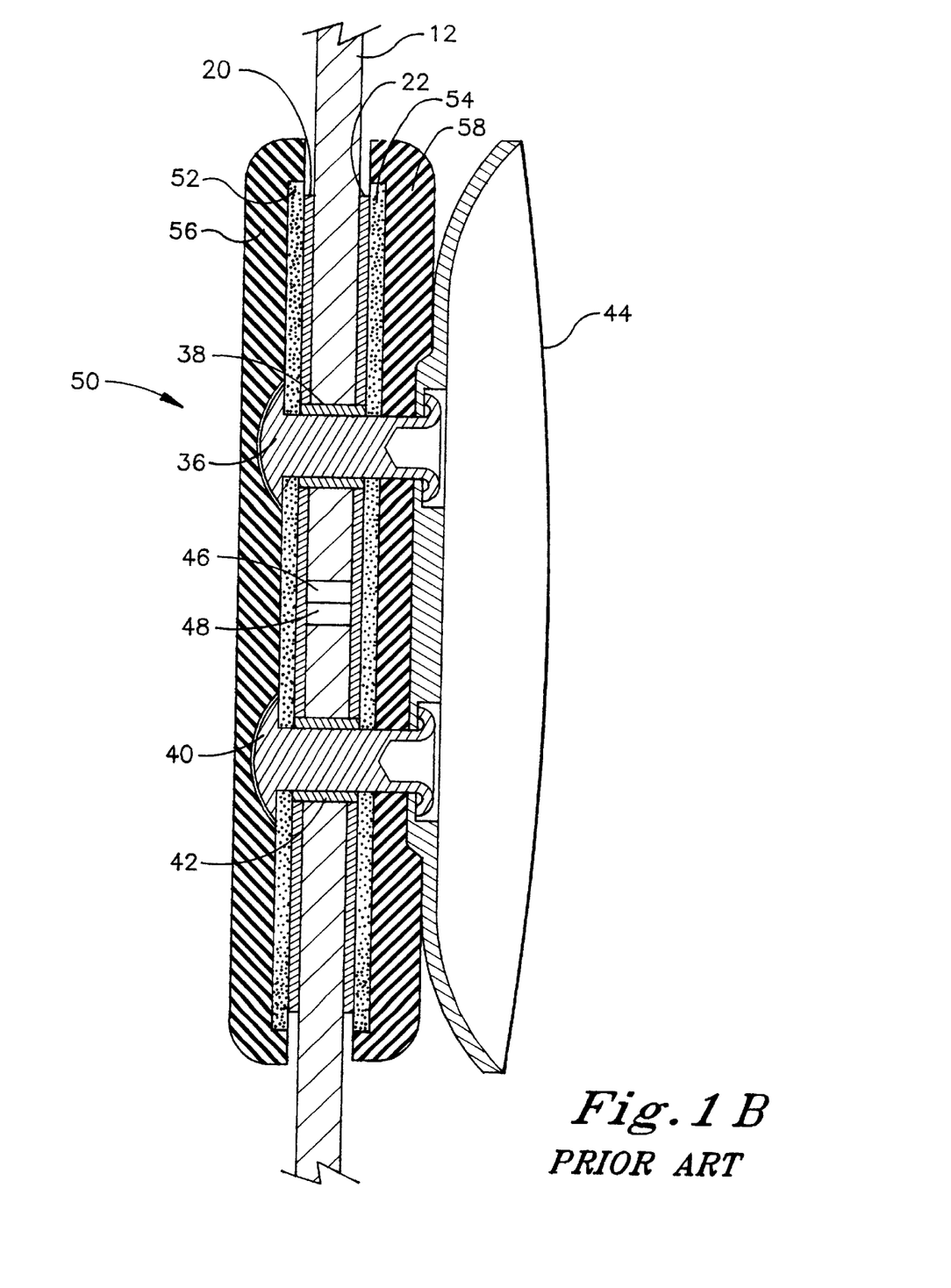
FIG. 1B is a cross-sectional view of an alternate prior art hinge for an orthopedic brace.

Referring to FIG. 1B, an alternate conventional hinge 50 is illustrated, wherein components of the hinge 50 common to the hinge 10 are designated by the same reference characters. The conventional hinge 50 is substantially identical to the conventional hinge 10, however, the flanges are omitted from the first and second hinge plates 52, 54 of the hinge 50. Instead the first and second hinge covers 56, 58 are permanently affixed to the first and second hinge plates 52, 54, respectively, by gluing.

Because orthopedic braces are commonly worn by athletes and other participants in active endeavors, orthopedic braces are preferably designed to be as unobtrusive as possible while performing their intended function. In particular, orthopedic braces are desirably designed to be compact and free of protruding components that could injure or irritate the user of the orthopedic brace or others coming in contact with the user. In addition, orthopedic braces are desirably designed to have lower production costs in response to cost sensitivities in the health care industry. Accordingly, it is an object of the present invention to provide a hinge for an orthopedic brace that provides effective rotational pivoting movement of the brace. It is another object of the present invention to provide such a hinge that has diminished size and has relatively smooth exterior surfaces. It is yet another object of the present invention to provide such a hinge having a simplified design that reduces material and assembly costs, thereby reducing the overall cost of the hinge and associated orthopedic brace. These objects and others are achieved by the present invention described hereafter.

SUMMARY OF THE INVENTION

The present invention is a hinge for an orthopedic brace, wherein the brace has an upper arm and a lower arm pivotally coupled by the hinge. The hinge comprises a first hinge plate having a substantially planar rigid support member with a first side and a second side. An inner friction-reducing covering is positioned on the first side and an outer protective covering is positioned on the second side. The inner friction-reducing covering and the outer protective covering are integrally formed to substantially enclose the support member in a single smooth continuous unitary covering. The inner friction-reducing covering reduces friction between the first hinge plate and the upper and lower arms during pivoting movement of the hinge and the outer protecting covering protects the hinge from external interference during pivoting movement and avoids injury to the user or others contacting the hinge. A second hinge plate having substantially the same construction as the first hinge plate is parallely aligned with the first hinge plate and is connected thereto. The lower end of the upper arm and the upper end of the lower arm are positioned between the first and second hinge plates and are rotatably connected thereto to provide pivotal coupling of the ends.

The support member of each hinge plate is formed from a first material and the unitary covering of the hinge plate is formed from a second material, wherein the friction coefficient of the second material with respect to the lower and upper ends is substantially less than that of the first material with respect to the lower and upper ends. The first material is preferably a metal and the second material is preferably a plastic. The hinge plate is preferably formed by an insert molding process, wherein the support member is inserted in a mold and a liquid plastic is injected into the mold around the support member. The liquid plastic is then hardened to a solid plastic forming the unitary covering and the hinge plate is removed from the mold. The support member may be provided with one or more securing bores formed therethrough. The securing bores receive the liquid plastic during the insert molding process. The plastic therein forms integral connective members between the inner and outer coverings upon hardening that secure the unitary covering to the support member. The present invention will be further understood, both as to its structure and operation, from the accompanying drawings, taken in conjunction with the accompanying description, in which similar reference characters refer to similar parts.

DESCRIPTION OF PREFERRED EMBODIMENTS

Figure 2:
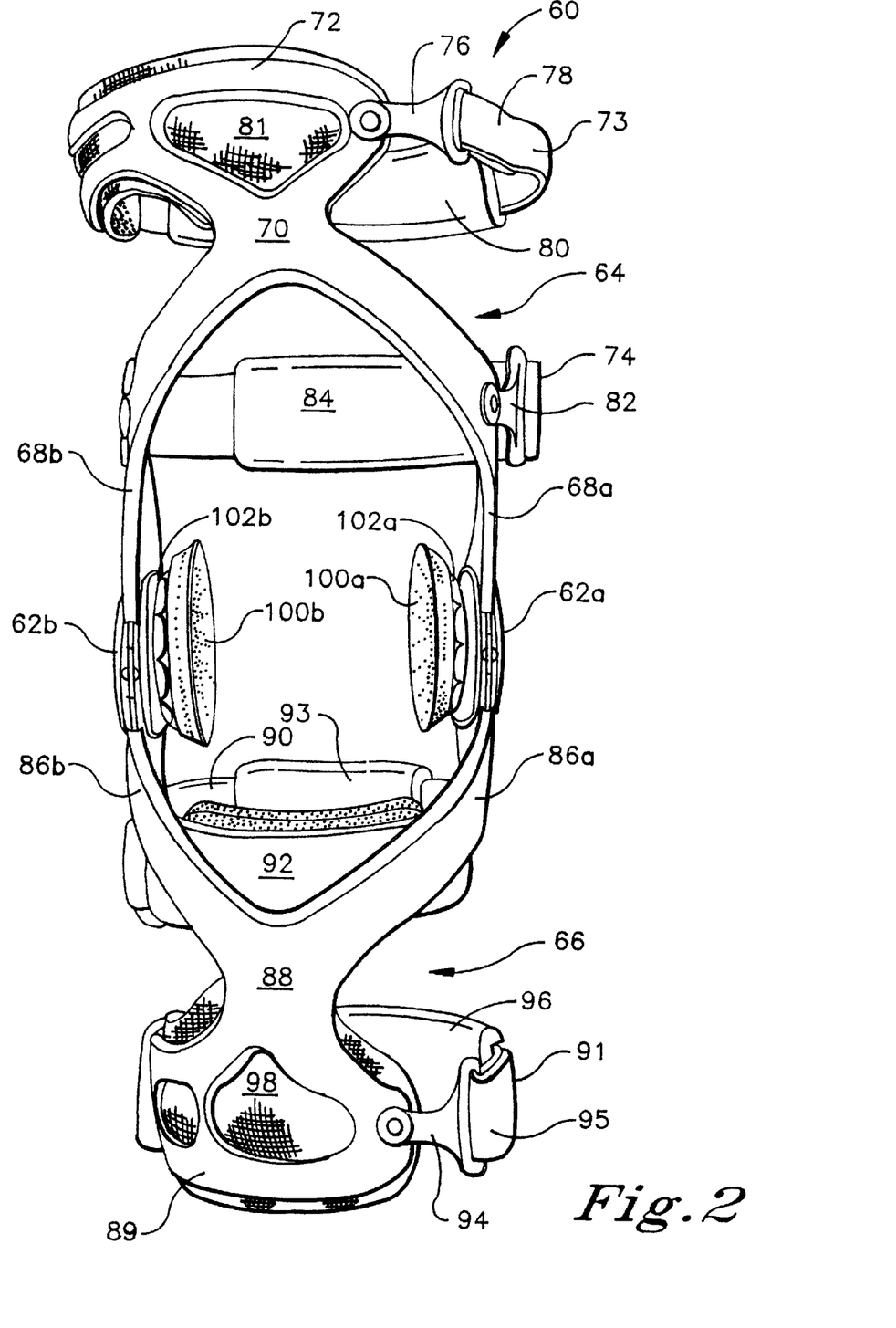
FIG. 2 is a frontal view of an orthopedic brace incorporating the hinges of the present invention.

Referring initially to FIG. 2, an orthopedic brace is generally designated 60. For purposes of illustration, the orthopedic brace 60 shown and described herein is a knee brace mountable on the right leg (not shown) of a human body, although it is understood that the skilled artisan can readily adapt the orthopedic brace 60 for mounting on the opposite leg or other joints of the body in accordance with the instant teaching. The orthopedic brace 60 comprises a plurality of components including a medial hinge 62a and a lateral hinge 62b having substantially the same construction embodying the hinge of the present invention. While the orthopedic brace 60 shown herein has both medial and lateral hinges 62a, 62b, it is apparent to the skilled artisan that the orthopedic brace can alternatively employ a single hinge in either the medial or lateral position.

The orthopedic brace 60 further comprises an upper brace assembly 64 and a lower brace assembly 66 opposingly positioned about the medial and lateral hinges 62a, 62b. The upper brace assembly 64 includes upper medial and lateral arms 68a, 68b, each having a lower proximate end rotatably coupled by the medial and lateral hinges 62a, 62b, respectively. The medial and lateral arms 68a, 68b arc in an upwardly anterior direction to form a first upper anterior cross member 70. The upper brace assembly 64 also includes a second upper anterior cross member 72 located above the first upper anterior cross member 70. The upper brace assembly 64 extends substantially the length of the upper leg of the user and is retained in removable engagement with the upper leg by means of first and second upper adjustable straps 73, 74. The first upper adjustable strap 73 includes a pivotable loop fixture 76 rotatably anchored to the second upper anterior cross member 72. A self-connecting strap end 78 is threaded through the pivotable loop fixture 76 and connected to itself. A posterior pad 80 provides a cushion between the first upper adjustable strap 73 and the posterior of the user's upper leg. An anterior pad 81 provides a cushion between the upper anterior cross members 70, 72 and the anterior of the user's upper leg. The second upper adjustable strap 74 engages the upper medial and lateral arms 68a, 68b below the first upper adjustable strap 73 and includes a pivotable loop fixture 82 and a posterior pad 84.

The lower brace assembly 66 includes lower medial and lateral arms 86a, 86b, each having an upper proximate end rotatably coupled by the medial and lateral hinges 62a, 62b, respectively. The medial and lateral arms 86a, 86b arc in a downwardly anterior direction to form a first lower anterior cross member 88. The lower brace assembly 66 also includes a second lower anterior cross member 89 located below the first lower anterior cross member 88. The lower brace assembly 66 extends substantially the length of the lower leg of the user and is retained in removable engagement with the lower leg by means of first and second lower adjustable straps 90, 91 The first lower adjustable strap 90 engages the lower medial and lateral arms 86a, 86b above the second lower adjustable strap 91 and includes anterior and posterior pads 92, 93. The second lower adjustable strap 91 includes a pivotable loop fixture 94 rotatably anchored to the second lower anterior cross member 89. A self-connecting strap end 95 is threaded through the pivotable loop fixture 94 and connected to itself. A posterior pad 96 provides a cushion between the second lower adjustable strap 91 and the posterior portion of the user's lower leg. An anterior pad 98 provides a cushion between the lower anterior cross members 88, 89 and the anterior portion of the user's lower leg.

As noted above, the lower adjustable straps 90, 91 attach the lower brace assembly 66 to the user's lower leg and the upper adjustable straps 73, 74 attach the upper brace assembly to the user's upper leg. Medial and lateral hinge pads 100a, 100b retained by medial and lateral hinge pad holders 102a, 102b are further provided to cushion the user's knee condyles from the hinges 62a, 62b. The medial and lateral hinge pads 100a, 100b, in association with pads 80, 81, 84, 92, 93, 96, 98 improve both the fit and the comfort of the orthopedic brace 60 during use.

Figure 3:
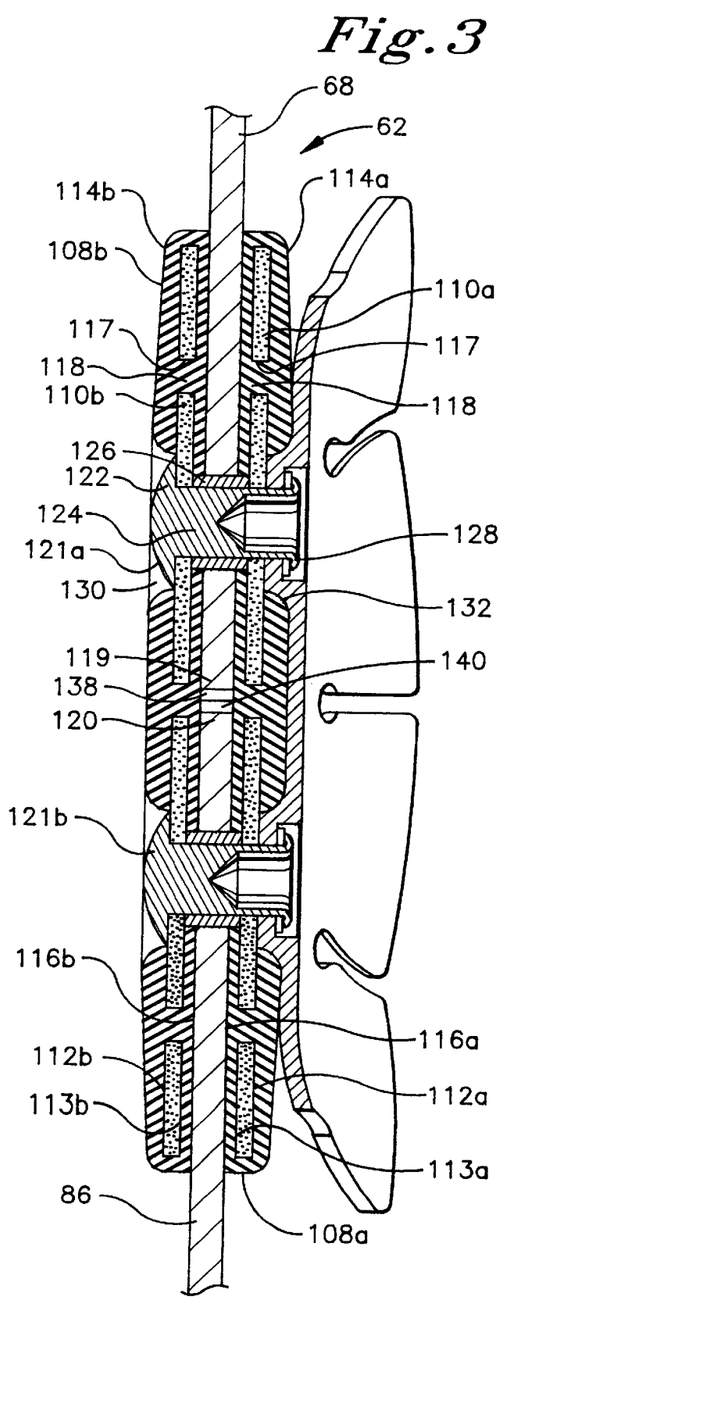
FIG. 3 is a cross-sectional view of a hinge of FIG. 2.
Figure 4:
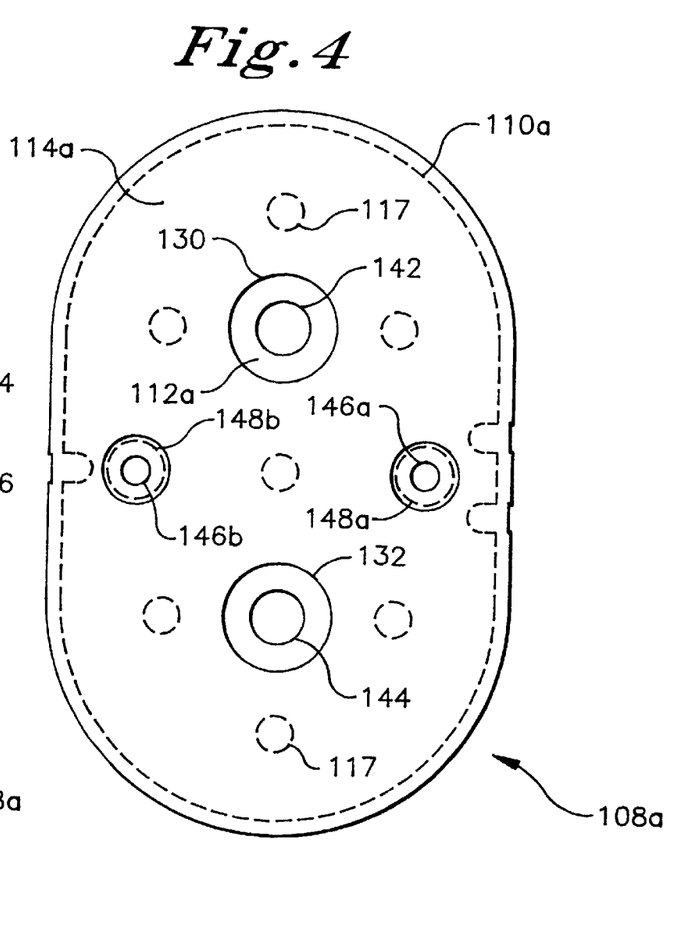
FIG. 4 is a frontal view of a hinge plate employed in a hinge of FIG. 2.
Figure 5:
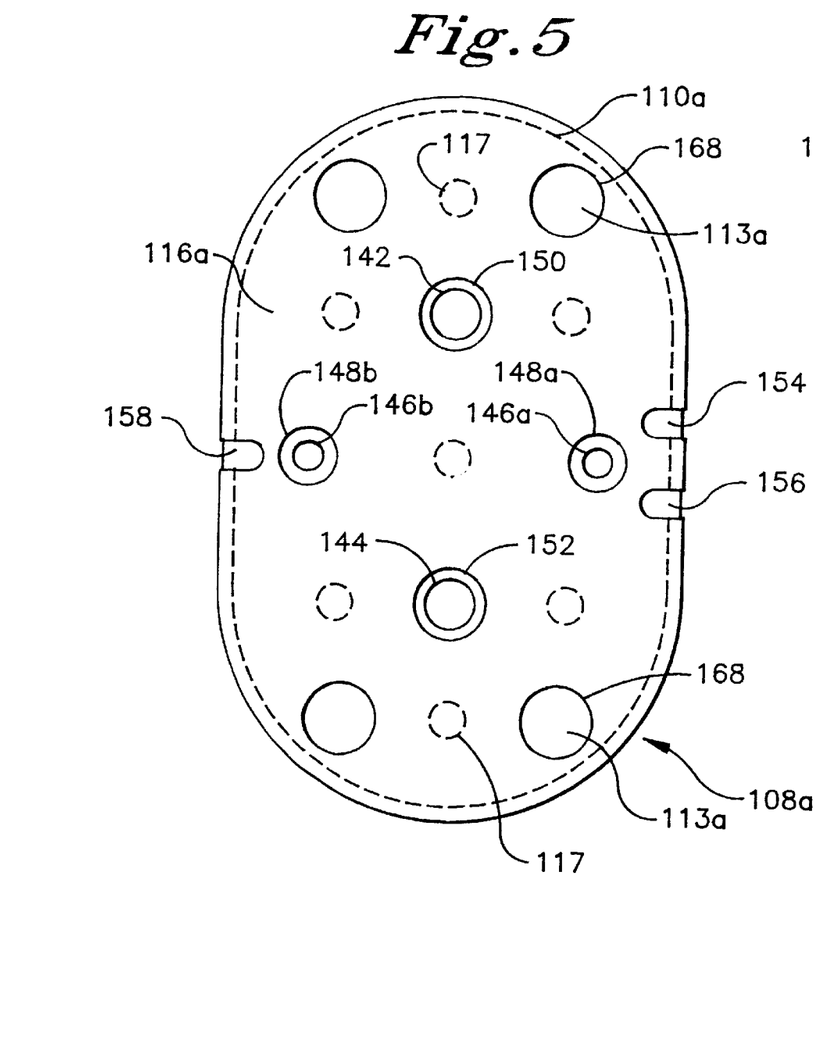
FIG. 5 is a rear view of the hinge plate employed in a hinge of FIG. 2.

Referring to FIGS. 3, 4, and 5, a hinge 62 of the present invention is illustrated in greater detail. It is understood that the hinge 62 shown in FIG. 3 is identical to the hinges 62a, 62b shown in FIG. 2. The hinge 62 includes a first hinge plate 108a and a second hinge plate 108b preferably having substantially the same construction. As can be seen in FIG. 3, the first and second hinge plates 108a, 108b have a low profile due to a substantially planar configuration. The first and second hinge plates 108a, 108b include substantially planar support members 110a, 110b having outer sides 112a, 112b and inner sides 113a, 113b. The support members 110a, 110b are preferably formed from a rigid, high-strength metal such as aluminum or steel. The first and second hinge plates 108a, 108b further include outer protective coverings 114a, 114b and inner friction-reducing coverings 116a, 116b preferably formed from a high-strength plastic providing a relatively smooth, low-friction surface.

Insofar as the first and second hinge plates 108a, 108b have substantially the same construction, their construction is described in further detail below with respect to the first hinge plate 108a. It is understood, however, that this description applies to the second hinge plate 108b as well. The outer protective covering 114a and the inner friction-reducing covering 116a are shown to be a single substantially continuous unitary covering integrally formed around and substantially enclosing the support member 110a. In a preferred embodiment, the outer and inner coverings 114a, 116a are integrally formed around the support member 110a by insert molding the support member 110a within the outer and inner coverings 114a, 116a. Insert molding comprises placing the support member 110a in a mold and injecting a fluid plastic into the mold to substantially surround the support member 110a. A plurality of securing bores 117 formed in the support member 110a are filled with plastic to form connective members 118 during the insert molding process that securely position the outer and inner coverings 114a, 116a relative to the support member 110a. Once the fluid plastic is in place in the mold, it is cured or hardened to a hard solid plastic and the resulting first hinge plate 108a is removed from the mold.

The upper and lower arms 68, 86 have lower and upper ends 119, 120 that are oriented proximal to the knee joint. The upper and lower arms 68, 86 are attached to the hinge 62 by conventional upper and lower fasteners 121a, 121b, such as the fastening rivets shown here having an identical construction. The fasteners 121a, 121b each have a head portion 122, a cylindrical portion 124 positioned within a bushing 126 upon which the upper and lower arms 68, 86 rotate, and a flange portion 128. The hinge plate 108a includes bores 130, 132 in the outer protective covering 114a that provide clearance for the head portion 122 and the flange portion 128 of the fasteners 121a, 121b. In use, the head portion 122 and flange portion 128 of the fasteners 121a, 121b are preferably flush with the outer protective covering 114a. The upper and lower arms 68, 86 preferably include intermeshing teeth 138,140 that meet at a contact point between the lower and upper ends 119, 120. The intermeshing teeth 138,140 maintain symmetric movement of the upper and lower brace assemblies 64, 66 relative to the hinge 62 in a conventional manner.

Referring to FIG. 4, a frontal view of the first hinge plate 108a is illustrated. The support member 110a is shown to further include circular bores 142, 144 for receiving the cylindrical portions 124 and bushings 126 of the fasteners 121a, 121b. Bores 146a, 146b are also provided in the midportion of the outer protective covering 114a and the inner friction-reducing covering 116a that, in association with bores 148a, 148b provided in the midportion of the support member 110a, receive a second fastener, such as a threaded screw (not shown), to secure the flexion and extension limiters (not shown) described hereafter. It is noted that the peripheral edge of the support member 110a does not extend fully to the peripheral edge of the first hinge plate 108a. Consequently the outer and inner coverings 114a, 116a define the peripheral edge of the first hinge plate 108a.

Referring to FIG. 5, a rear view of the first hinge plate 108a is illustrated. The inner friction-reducing covering 116a is shown to further include bores 146a, 146b, 150, 152 and grooves 154, 156, 158. The grooves 154, 156, in combination with the bore 146a in the inner friction-reducing covering 116a, the bore 148a in the support member 110a and a fastener, such as a threaded screw (not shown), securely position a flexion limiter that will be described hereafter with reference to FIGS. 7 and 8. The groove 158, in combination with the bore 146b in the inner friction-reducing covering 116a, the bore 148a in the support member 110a and a fastener, such as a threaded screw (not shown), securely position an extension limiter that will be described hereafter with reference to FIGS. 6 and 8. The inner friction-reducing covering 116a also includes bores 168 formed as a result of the insert molding process.

Figure 6:
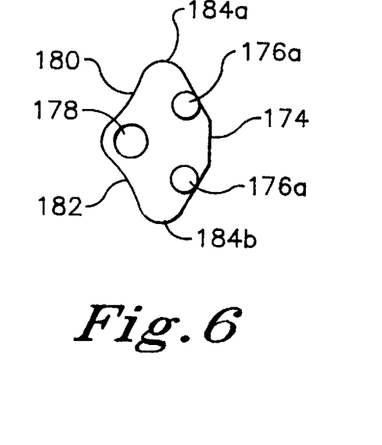
FIG. 6 is a frontal view of an extension limiting device employed in a hinge of FIG. 2.
Figure 8:
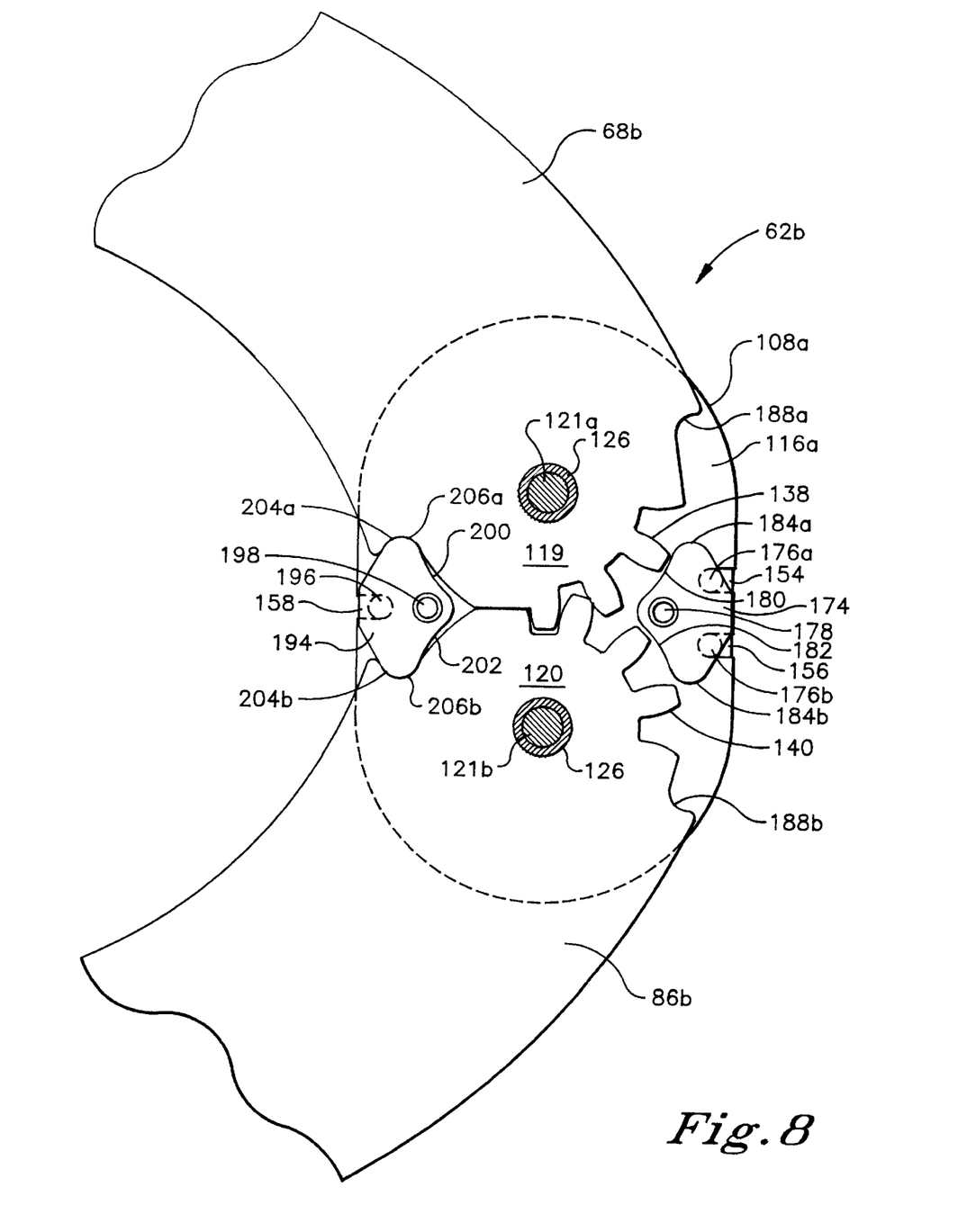
FIG. 8 is a frontal cut away view of a hinge of FIG. 2.

Referring to FIGS. 6 and 8, wherein the hinge plate 108b of hinge 62b in FIG. 8 is removed for clarity, the extension limiter 174 is illustrated having pins 176a, 176b and a bore 178 that help position and secure the extension limiter 174 between the first and second hinge plates 108a, 108b. The pins 176a, 176b extend from the surface of the extension limiter 174 and are aligned with and inserted into the grooves 154, 156 formed in the first and second hinge plates 108a, 108b. A fastener, such as a threaded screw (not shown), is inserted into the bores 146b, 148b in the first and second hinge plates 108a, 108b and the bore 178 in the extension limiter 174. Thus, the extension limiter 174 is inserted and secured between the first and second hinge plates 108a, 108b or is removed as desired. In operation, first and second arcuate surfaces 180, 182 provide clearance for rotary movement of the lower end 119 of the upper brace assembly 64, the upper end 120 of the lower brace assembly 66 and the intermeshing teeth 138, 140. The first and second stop surfaces 184a, 184b abut anterior arm stop surfaces 188a, 188b of the upper and lower brace assemblies 64, 66 to limit extension of the user's leg. Alternate extension limiters can be provided, wherein the position of the stop surfaces 184a, 184b relative to the pins 176a, 176b differs from that shown to provide increased or decreased extension limits. Alternate extension limiters can also be provided, wherein the position of the arm stop surfaces 188a, 188b differs relative to the upper and lower arms 68a, 68b, 86a, 86b.

Figure 7:
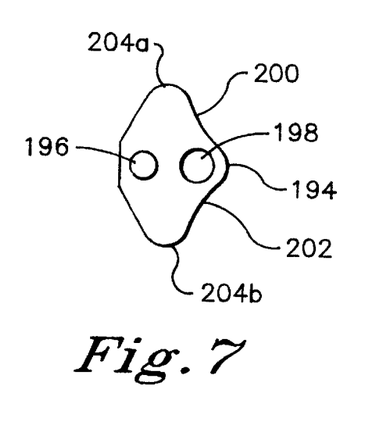
FIG. 7 is a frontal view of a flexion limiting device employed in a hinge of FIG. 2.

Referring to FIGS. 7 and 8, the flexion limiter 194 is illustrated having a pin 196 and a bore 198 that help position and secure the flexion limiter 194 between the hinge plates 108a, 108b. The pin 196 extends from the surface of the flexion limiter 194 and is aligned with and inserted into the grooves 158 formed in the first and second hinge plates 108a, 108b. A fastener, such as a threaded screw (not shown), is inserted into the bores 146a, 148a in the first and second hinge plates 108a, 108b and the bore 198 of the flexion limiter 194. Thus, flexion limiter 194 is inserted and secured between the first and second hinge plates 108a, 108b or is removed as desired. In operation, first and second arcuate surfaces 200, 202 provide clearance for rotary movement of the lower end 119 of the upper brace assembly 64, the upper end 120 of the lower brace assembly 66 and the intermeshing teeth 138, 140. The first and second stop surfaces 204a, 204b abut posterior arm stop surfaces 206a, 206b on the upper and lower brace assemblies 64, 66 to limit flexion of the user's leg. Alternate flexion limiters can be provided, wherein the position of the stop surfaces 204a, 204b relative to the pin 196 differs from that shown to provide increased or decreased flexion limits.

In operation, a user mounts the orthopedic brace 60 onto the leg and secures the brace 60 with the straps 73, 74, 90 and 91. As the user flexes or extends the leg during activity, the upper and lower brace assemblies 64, 66 rotatably pivot relative to the hinges 62a, 62b. The intermeshing gears 138, 140 maintain symmetric movement of the upper and lower brace assemblies 64, 66 relative to the hinges 62a, 62b, thereby stabilizing movement of the knee joint. The inner friction-reducing coverings 116a, 116b substantially reduce friction between upper and lower brace assemblies 64 and 66 and the hinges 62a, 62b to facilitate the rotational pivoting movement of the brace 60. In particular, the inner friction-reducing coverings 116a, 116b preferably have a lower friction coefficient with respect to the ends of the arms 119, 120 than that of the support members 110a, 110b. The outer protective coverings 114a, 114b protect the hinges 62a, 62b from external interferences and provide smooth outer hinge surfaces that do not abrade the user or others contacting the hinges 62a, 62b during use of the brace 60. As can be appreciated by the skilled artisan, the hinge of the present invention achieves a reduced profile by integrating the internal support members and coverings while maintaining strength and functionality at a decreased cost.

While the particular hinge for an orthopedic brace shown and disclosed herein is fully capable of obtaining the objects and providing the advantages stated herein, it is understood that the hinge is merely illustrative of presently preferred embodiments of the invention and that other embodiments are possible within the scope of the present invention.

We claim:

1. A hinge for an orthopedic brace comprising:
  a hinge plate including a substantially planar rigid support member having a first side and a second side, a first covering on said first side, and a second covering on said second side, wherein said first and second coverings are integrally formed with one another from a solid insert molded plastic having a substantially smooth outer surface to provide a substantially continuous unitary covering substantially enclosing said support member.

2. A hinge as recited in claim 1 wherein said support member has a bore formed therein receiving said unitary covering.

3. A hinge as recited in claim 1 wherein said support member has a bore formed therethrough and said unitary covering has a connective member received through said bore, said connective member integrally formed with said first and second coverings and positioned therebetween.

4. A hinge as recited in claim 1 wherein said hinge plate is a first hinge plate, said support member is a first support member, and said unitary covering is a first unitary covering, said hinge further comprising a second hinge plate including a second substantially planar rigid support member having a third side and a fourth side, a third covering on said third side, and a fourth covering on said fourth side, wherein said third and fourth coverings are integrally formed with one another to provide a second substantially continuous unitary covering substantially enclosing said second support member, said second hinge plate connected to said first hinge plate.

5. A hinge as recited in claim 4 further comprising a lower end of an upper arm and an upper end of a lower arm positioned between said first and second hinge plates in rotatable engagement with said first and second hinge plates.

6. A hinge as recited in claim 1 further comprising a lower end of an upper arm and an upper end of a lower arm rotatably engaging said hinge plate.

7. A hinge as recited in claim 6 wherein said unitary covering has a substantially lower friction coefficient with respect to said lower and upper ends than said support member.

8. A hinge as recited in claim 1 wherein said support member is formed from a metal.

9. A hinge for an orthopedic brace formed by a process comprising the steps of:
  inserting a substantially planar rigid support member in a mold;
  injecting a fluid plastic into said mold to substantially enclose said support member;
  hardening said fluid plastic into a solid plastic forming a substantially continuous unitary covering; and
  removing a hinge plate from said mold comprising said support member substantially enclosed in said unitary covering, wherein said unitary covering has a substantially smooth outer surface, avoiding abrasion to a person contacting said outer surface.

10. A hinge formed by the process recited in claim 9 further comprising rotatably connecting a lower end of an upper arm and an upper end of a lower arm to said hinge plate.

11. A hinge formed by the process recited in claim 10 wherein said support member is formed from a rigid material and said solid plastic of said unitary covering has a substantially lower friction coefficient with respect to said lower and upper ends than said rigid material.

12. A hinge formed by the process recited in claim 11 wherein said rigid material is a metal.

13. A hinge formed by the process recited in claim 9, wherein said hinge plate is a first hinge plate, said support member is a first support member, and said unitary covering is a first unitary covering, the process further comprising:
  inserting a substantially planar rigid second support member in a mold;
  injecting a fluid plastic into said mold to substantially enclose said second support member;
  hardening said fluid plastic into a solid plastic forming a substantially continuous second unitary covering substantially enclosing said second support member; and
  removing a second hinge plate from said mold comprising said second support member substantially enclosed in said second unitary covering, wherein said second unitary covering has a substantially smooth outer surface, avoiding abrasion to a person contacting said outer surface of said second unitary covering.

14. A hinge formed by the process recited in claim 13 further comprising connecting said first and second hinge plates in parallel alignment and positioning a lower end of an upper arm and an upper end of a lower arm between said first and second hinge plates in rotatable engagement with said upper end and said lower end.

15. A hinge for an orthopedic brace comprising:
  a hinge plate including a substantially planar rigid support member having a first side and a second side, a first covering on said first side, and a second covering on said second side, wherein said first and second coverings are integrally formed with one another from a solid insert molded plastic having a substantially smooth outer surface to provide a substantially continuous unitary covering substantially enclosing said support member;
  a lower end of an upper arm rotatably connected to said hinge plate; and
  an upper end of a lower arm rotatably connected to said hinge plate, wherein said unitary covering has a substantially lower friction coefficient with respect to said lower and upper ends than said support member.

16. A hinge as recited in claim 15 wherein said support member is formed from a metal.

17. A hinge as recited in claim 15 wherein said hinge plate is a first hinge plate, said support member is a first support member, and said unitary covering is a first unitary covering, said hinge further comprising a second hinge plate including a second substantially planar rigid support member having a third side and a fourth side, a third covering on said third side, and a fourth covering on said fourth side, wherein said third and fourth coverings are integrally formed with one another from a solid insert molded plastic having a substantially smooth outer surface to provide a second substantially continuous unitary covering substantially enclosing said second support member, said second hinge plate connected to said first hinge plate.

18. A hinge as recited in claim 17 wherein said upper end and said lower end are positioned between said first and second hinge plates and said upper end and said lower end rotatably engage said second hinge plate.

* * * * *